United States Patent
Goldstein

(10) Patent No.: US 10,418,016 B2
(45) Date of Patent: Sep. 17, 2019

(54) METHODS AND DEVICES FOR ATTENUATING SOUND IN A CONDUIT OR CHAMBER

(71) Applicant: Staton Techiya, LLC, Delray Beach, FL (US)

(72) Inventor: Steven Wayne Goldstein, Delray Beach, FL (US)

(73) Assignee: Staton Techiya, LLC, Delray Beach, FL (US)

( * ) Notice: Subject to any disclaimer, the term of this patent is extended or adjusted under 35 U.S.C. 154(b) by 428 days.

(21) Appl. No.: 15/168,020

(22) Filed: May 28, 2016

(65) Prior Publication Data

US 2017/0040012 A1    Feb. 9, 2017

Related U.S. Application Data

(60) Provisional application No. 62/168,703, filed on May 29, 2015.

(51) Int. Cl.
| | |
|---|---|
| *G10K 11/165* | (2006.01) |
| *A61F 11/10* | (2006.01) |
| *H04R 1/10* | (2006.01) |
| *G10K 11/16* | (2006.01) |
| *A61F 11/06* | (2006.01) |

(52) U.S. Cl.
CPC ............ *G10K 11/165* (2013.01); *A61F 11/10* (2013.01); *H04R 1/1016* (2013.01)

(58) Field of Classification Search
CPC ........ G10K 11/165; A61F 11/10; A61F 11/06; H04R 1/1016
See application file for complete search history.

(56) References Cited

U.S. PATENT DOCUMENTS

| | | | |
|---|---|---|---|
| 4,091,892 | A | 5/1978 | Hehmann et al. |
| 6,082,487 | A | 7/2000 | Angelo et al. |
| 6,343,672 | B1 | 2/2002 | Petela et al. |
| 6,354,398 | B1 | 3/2002 | Angelo et al. |
| 6,491,134 | B2 | 12/2002 | Ryan et al. |

(Continued)

FOREIGN PATENT DOCUMENTS

WO    WO 2014039026 A1 *    3/2014    ............. A61F 11/10

*Primary Examiner* — Edgardo San Martin
(74) *Attorney, Agent, or Firm* — Akerman LLP; Peter A. Chiabotti; Mammen (Roy) P. Zachariah, Jr.

(57) ABSTRACT

Occlusion devices, earpiece devices and methods of forming occlusion devices are provided. An occlusion device is configured to occlude an ear canal, but other biological and non-biological conduits or chambers can be occluded using the devices and methods herein. The occlusion device includes an insertion element and at least one occluding member or element (which can be expandable) disposed on the insertion element. The occluding member is configured to receive a medium via the insertion element and is configured to expand, responsive to the medium, to contact the ear canal. Alternatively, the occluding member is made of a non-Newtonian fluid and can be enclosed by a balloon or not. Physical parameters of the occlusion device are selected to produce a predetermined sound attenuation characteristic over a frequency band. Use of a non-Newtonian fluid provides additional options or variables in customizing or designing a predetermined sound attenuation characteristic.

20 Claims, 12 Drawing Sheets

(56) References Cited

U.S. PATENT DOCUMENTS

| | | |
|---|---|---|
| 7,347,824 B2 | 3/2008 | Wilkinson et al. |
| 7,476,056 B2 | 1/2009 | Dreyer |
| 7,551,062 B2 | 6/2009 | Croft, III et al. |
| 7,700,111 B2 | 4/2010 | Miller et al. |
| 7,708,697 B2 | 5/2010 | Wilkinson et al. |
| 7,850,618 B2 | 12/2010 | Wilkinson et al. |
| 7,866,442 B2 | 1/2011 | Shimomura et al. |
| 7,921,966 B2 | 4/2011 | Chiou et al. |
| 8,118,031 B2 | 2/2012 | Seville |
| 8,196,704 B2 | 6/2012 | Chiou et al. |
| 8,201,569 B2 | 6/2012 | Goodyear et al. |
| 8,208,652 B2 * | 6/2012 | Keady ............... A61F 11/08 381/328 |
| 8,229,128 B2 * | 7/2012 | Keady ............... A61F 11/08 381/322 |
| 8,312,960 B2 * | 11/2012 | Keady ............... A61F 11/10 181/135 |
| 8,327,973 B2 | 12/2012 | Parish et al. |
| 8,522,916 B2 * | 9/2013 | Keady ............... A61F 11/10 181/135 |
| 8,550,206 B2 * | 10/2013 | Keady ............. H04R 25/656 181/135 |
| 8,631,801 B2 * | 1/2014 | Keady ............... A61F 11/10 128/865 |
| 8,678,011 B2 * | 3/2014 | Goldstein ........... A61F 11/10 128/864 |
| 9,123,323 B2 * | 9/2015 | Keady .............. H04R 9/027 |
| 9,169,750 B2 | 10/2015 | Disimile |
| 9,247,858 B2 | 2/2016 | Goodyear et al. |
| 9,333,116 B2 | 5/2016 | Bauman |
| 9,539,147 B2 * | 1/2017 | Keady ............... A61F 11/10 |
| 2001/0030079 A1 | 10/2001 | Ryan |
| 2003/0120182 A1 | 6/2003 | Wilkinson et al. |
| 2004/0247570 A1 | 12/2004 | Miller |
| 2006/0037615 A1 | 2/2006 | Wilkinson et al. |
| 2006/0070623 A1 | 4/2006 | Wilkinson et al. |
| 2006/0252761 A1 | 11/2006 | Davis et al. |
| 2008/0006478 A1 | 1/2008 | Dreyer |
| 2008/0129470 A1 | 6/2008 | Croft et al. |
| 2008/0154145 A1 | 6/2008 | Wilkinson et al. |
| 2010/0186785 A1 | 7/2010 | Goodyear et al. |
| 2011/0031059 A1 | 2/2011 | Parish et al. |
| 2011/0160279 A1 | 6/2011 | Ramkumar et al. |
| 2012/0247521 A1 | 10/2012 | Goodyear et al. |
| 2013/0123919 A1 * | 5/2013 | Goldstein ............ A61F 2/18 623/10 |
| 2014/0146989 A1 * | 5/2014 | Goldstein ........... A61F 11/08 381/380 |
| 2014/0155688 A1 * | 6/2014 | Goldstein ........... A61F 11/10 128/865 |
| 2014/0373854 A1 * | 12/2014 | Keady ............... A61F 11/10 128/865 |
| 2016/0008176 A1 * | 1/2016 | Goldstein ........... A61F 11/10 128/864 |
| 2016/0129246 A1 | 5/2016 | Housley et al. |
| 2016/0295311 A1 * | 10/2016 | Keady ............. H04R 25/652 |

* cited by examiner

Schematic of particles forming hydroclusters under shear

METHODS AND DEVICES FOR ATTENUATING SOUND IN A CONDUIT OR CHAMBER

CROSS REFERENCE TO RELATED APPLICATIONS

This Application is a utility patent application that claims the priority benefit of Provisional Patent Application No. 62/168,703 entitled "METHODS AND DEVICES FOR ATTENUATING SOUND IN A CONDUIT OR CHAMBER" filed on May 29, 2015, the entire contents of which is incorporated herein by reference in its entirety.

FIELD

The present embodiments relate to occluding elements used for attenuating sound or isolating sound from a closed conduit or chamber such as an ear canal.

BACKGROUND OF THE INVENTION

Non-Newtonian fluids and more particularly, shear thickening fluids are being considered and investigated for potential commercial use as materials for liquid body armour or protective clothing due to their unique properties. The primary focus of the investigations have revolved around adaptive stiffness and dampening properties that can prevent ballistic weapons or sharp knives or stakes from penetrating a piece of body armour or protective clothing.

People may be exposed to noise pollution from their ambient environment (for example, from traffic, from construction sites, from aircraft, etc.). People may also be intentionally exposed to high sound levels (for example, from cell phones, MP3 players, home theater equipment, rock concerts, etc.). Studies have shown that ear damage, which may lead to permanent hearing impairment, is not only increasing in the general population, but may be increasing at a significantly faster rate in younger populations. The potential for noise induced hearing loss (NIHL) may be a function of both a level and a duration of exposure to a sound stimulus. Studies have also indicated that hearing damage is a cumulative phenomenon. Although hearing damage due to industrial or background noise exposure is more thoroughly understood, there may also be a risk of hearing damage from the exposure to intentional excessive noise, such as with the use of headphones.

Devices which attenuate sound directly to the ear canal are known. Conventional devices typically fit in the ear, around the ear and/or beyond the ear. Examples of these devices include headphones, headsets, earbuds and hearing aids. Earpieces that occlude the ear canal may provide increased attenuation of the ambient environment, offering improved sound isolation. However, conventional in-ear, in-concha or in canal earpieces may be fitted for a cross-section of a population and may not provide adequate sound isolation. Conventional in-ear, in-concha or in canal earpieces, thus, may not be properly fitted to the individual user and may not be adequately sealed, leading to reduced sound attenuation of the ambient environment. Furthermore, even if property fitted, as the ambient environment becomes louder, the effectiveness of the existing materials used for sound attenuating or isolation in-ear earpiece (or other devices fitting outside the ear) may not provide adequate protection. Most often, they are static in their attenuation properties, whereby the maximum attenuation is provided regardless of the ambient sound level.

SUMMARY

The present embodiments can be embodied in a sound attenuating device, including an occluding element configured to form a closed conduit or chamber upon insertion into an open end of the conduit or chamber and the inclusion of non-Newtonian fluid forming at least a portion of the occluding element where the non-Newtonian fluid provides an increasing (or variable) attenuation response in response to an increasing sound pressure leveling impinging an surface exposed to the ambient environment of the occluding member. In some embodiments, the non-Newtonian fluid is a shear thickening fluid or a dilatant fluid and where the non-Newtonian fluid includes carrier liquid and rigid colloidal particles. In some embodiments, the non-Newtonian fluid can include carrier fluid selected from the group of water, ethylene glycol (EG) and the non-Newtonian fluid further includes particles, microspheres, and or microfibers selected from the group comprising silica, titanium, oxide, calcium carbonate, cornstarch, synthetically occurring minerals, naturally occurring minerals, polymers, glass, stainless steel or a mixture of any of the aforementioned particles. In some embodiments, the non-Newtonian fluid is a shear thickening fluid containing composites using rubber as a precursor and adding a catalyzing agent. In yet other variant embodiments, the first member is formed (or includes) using a shear thickening fluid combined with an open cell polyurethane to form a foam-shear thickening fluid composite. In yet other embodiments, the non-Newtonian fluid is a non-particle based shear thickening fluid. Examples of non-particle based shear thickening fluid can include poly vinyl alcohol containing boric acid or poly dimethylsiloxane containing boric acid. In some embodiments, the non-Newtonian fluid comprises anisotropic particles, spherical particles, or at least one of fibers, rod-like elements, nanoparticles, or nano-tubes. The non-Newtonian fluid can also be electrorheological fluids composed of dispersions of electrically polarizable particles in an insulating fluid that increases in shear viscosity when exposed to an electric field. Alternatively, the non-Newtonian fluid can also be magnetorheological fluids composed of dispersions of magnetic particles in an inert or non-magnetic carrier liquid that increases in shear viscosity when exposed to a magnetic field. In some embodiments, the first member can include a balloon filled with the non-Newtonian fluid. In some embodiments, the sound attenuating device is an earpiece configured to occlude an ear canal with the occluding element. In some embodiments, the sound attenuating device can further include an ear canal receiver and an ear canal microphone configured to reside in a sealed area when the occluding element is placed within an orifice or external opening of the ear canal. Note that the ear canal is just one example of a conduit or cavity that can be closed or occluded using the method and devices disclosed herein. Other biological and non-biological conduits can equally benefit from the methods and devices disclosed or claimed herein.

The present embodiments can also include a method of attenuating sound in a conduit or chamber. The method can include providing a open-ended conduit or chamber and forming a closed conduit or chamber using at least a first member that includes a non-Newtonian fluid where the first member is placed at an open end of the conduit or chamber and where the non-Newtonian fluid provides an increasing attenuation response in response to an increasing sound pressure level impinging an outer surface of the first member. The non-Newtonian fluid can include any of the fluids or particles or elements described above and in any combinations or permutation thereof. Furthermore, embodiments herein can increase the attenuation based on the ambient SPL, thus providing users the ability to maintain situational awareness without having to remove a protective device (such as an earpiece or headphone) in non-hostile acoustic environments. In other words, embodiments herein maintain situational awareness in a passive manner without the use of active components or electronics. The chemistry of the non-Newtonian fluid enables a dynamic or variable attenuation characteristic that can be tailored or configured by a designer with an increasing number of variables as explained further below. The non-Newtonian fluid can replace or enhance conventional headset materials (such as rubber or foam) or otherwise be incorporated into earpieces, headsets, or headphones to enhance the attenuation efficacy of such devices based on the ambient SPL. In other words, using non-Newtonian fluids, the greater the ambient SPL, the greater the attenuation properties of the earpiece, headset, earphone or earplug. This characteristic is in sharp contrast to the rubber, foam, and/or paraffin used in typical earpieces used for NIHL protection or other purposes. Non-Newtonian fluids provide for variable attenuation, rather than a static or fixed level of attenuation exhibited by existing products. The non-Newtonian fluids provide a maximum amount of acoustic protection regardless of the acoustic conditions such that the louder the acoustic conditions the greater the attenuation the earpiece (or other device using the non-Newtonian fluid) offers. The non-dynamic aspect of conventional products such as foam only provides a static amount of attenuation.

Thus, embodiments herein using non-Newtonian fluids can provide situation awareness without the additional use of active electronics. With conventional products such as an existing foam earplug, a user would need to remove the earplug in quiet conditions to hear ones voice in a non-hostile acoustic environment whereas the non-Newtonian embodiments herein become more acoustically transparent at low sound pressure levels (e.g., 75 dB) and increases its acoustical impendence (attenuation) as the sound pressure level above 75 dB is increased. Thus, the user in conditions where the volume is comfortable does not need to pull the product out of their ear. The non-Newtonian embodiments herein can be designed to have no or reduced attenuation such that all acoustic acuity is preserved below a predetermined sound pressure level (such as 75 dB). Furthermore, the behavior of a product incorporating non-Newtonian fluids can be designed to be instantaneous such that attenuation occurs immediately once a certain sound pressure level (shearing force) reaches the exposed material. The non-Newtonian fluids can also be designed such that the exposed material can then immediately become flaccid once the sound pressure level drops below a certain sound pressure level. In yet other embodiments, the non-Newtonian fluids can be designed or configured or combined with other materials to exhibit a delayed transition to a flaccid state after hardening or exhibit a delayed transition to a hardened state after being in a flaccid state.

BRIEF DESCRIPTION OF THE DRAWINGS

The invention may be understood from the following detailed description when read in connection with the accompanying drawing. It is emphasized, according to common practice, that various features of the drawings may not be drawn to scale. On the contrary, the dimensions of the various features may be arbitrarily expanded or reduced for clarity. Moreover, in the drawing, common numerical references are used to represent like features. Included in the drawing are the following figures.

DETAILED DESCRIPTION OF THE INVENTION

Aspects of the present embodiments include methods and devices for occluding an ear canal which provide a predetermined sound attenuation characteristic over various parameters. For example, the predetermined sound attenuation characteristic can be over a sound pressure level impinging on a surface of an occluding member such as a balloon containing (or incorporating) non-Newtonian fluid or a member that is just made of the non-Newtonian fluid. Using the non-Newtonian fluid, the attenuation characteristic will likely provide for greater attenuation as the sound pressure level (SPL) in an ambient field that impinges on the exterior surface of the non-Newtonian fluid. If the non-Newtonian fluid is a shear thickening fluid (STF), the higher SPL or higher volume would cause the STF to become more viscous and harder, thereby providing greater sound attenuation properties in the material itself as a sound gets louder. In other words, as the sound volume exposure to the material increases, the greater sound attenuating properties the material (made of STFs) will provide as a result of the shear thickening effect that STFs provide. Normally, this is considered a benefit for reducing penetration by ballistic weapons such as bullets or for knives, but STFs and non-Newtonian fluids further provide the acoustic benefit of sound attenuation. Of particular benefit is the increased attenuation provided as the volume or SPL exposure becomes greater. The STFs may also provide predetermined attenuation characteristics over other parameters such as over a frequency band, such that sound is attenuated more in one frequency range than in another frequency range of the frequency band. Exemplary earpiece devices of the present embodiments include an occlusion section or member that can be part of an earpiece. The Occlusion member can be a balloon or expandable member filled with non-Newtonian fluid or STFs or the occlusion member can just be a non-Newtonian fluid itself. In one embodiment, it can be composed of material similar to "Silly Putty"™ by Crayola, LLC. Silly Putty is based on silicone polymers that have unusual physical properties. It bounces, but breaks when given a sharp blow and can also flow like a liquid. It contains a viscoelastic liquid silicone, a type of non-Newtonian fluid, which makes it act as a viscous liquid over a long time period but as an elastic solid over a short time period. If a balloon or expandable element is used, it can be configured to receive a medium such as the non-Newtonican fluid and to expand to contact and conform to the ear canal. The sound attenuation characteristic of the earpiece device may be selected based on physical parameters of the occlusion member.

Figure 1:
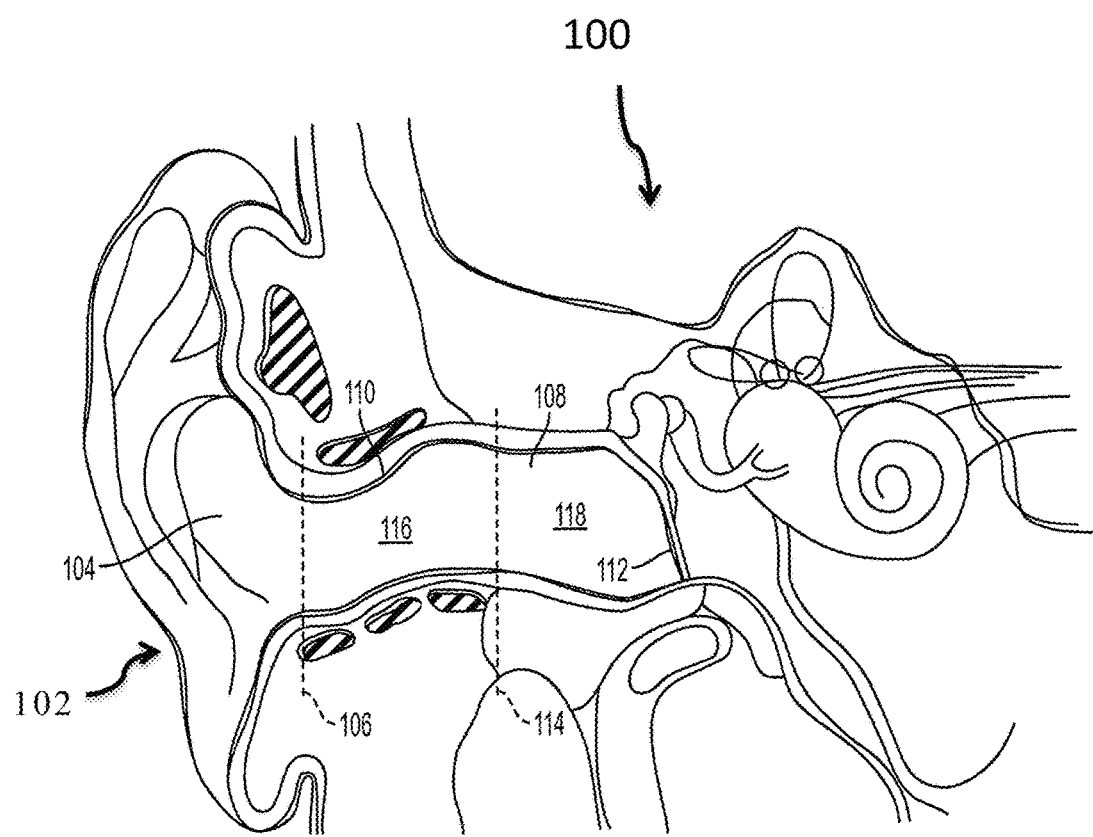
FIG. 1 is a cross section diagram of an ear illustrating a general physiology of the ear.

Referring to FIG. 1, a cross section diagram of ear 100 is shown, which illustrates the general physiology of ear 100. An external portion of ear 100 includes pinna 102 and concha 104. An internal portion of ear 100 includes ear canal 108 and tympanic membrane 112.

Pinna 102 is a cartilaginous region of ear 100 that focuses acoustic information from an ambient environment to ear canal 108. Concha 104 is a bowl shaped region in proximity to ear canal opening, indicated by dashed line 106.

Wall 110 (also referred to herein as ear canal wall 110) of ear canal 108 forms an acoustic chamber, which terminates with tympanic membrane 112. Sound enters ear canal 108 (at dashed line 106) and is subsequently received by tympanic membrane 112. Tympanic membrane 112 is a flexible membrane in the middle ear that couples to components of the inner ear. In general, acoustic information resident in ear canal 108 vibrates tympanic membrane 112. The vibration is converted to a signal (corresponding to the acoustic information) that is provided to an auditory nerve.

Ear canal 108 typically includes cartilaginous region 116 (between dashed lines 106 and 114) and bony region 118 (between dashed line 114 and tympanic membrane 112). Cartilaginous region 116 includes a layer of cartilage underlying the skin layer. Bony region 118 represents an area where bone underlies ear canal wall 110. Vibrations may be conducted through the bone (in bony region 118), pass through ear canal wall 110, and may be radiated as sound into ear canal 108.

In bony region 118, a skin layer of ear canal wall 110 may be sensitive to pressure. In general, the skin layer in bony region 118 is approximately one tenth a thickness of a skin layer in ear cartilaginous region 116. Thus, in bony region 118, there is little tissue separating skin from bone. Accordingly, placement of an object (such as an earplug) in bony region 118 can stimulate nerves (due to skin being pressed against bone), which can be uncomfortable and even induce significant pain.

In contrast to bony region 118, cartilaginous region 116 is a highly flexible region having no substantial rigid structure. Thus, cartilaginous region 116 may be more easily deformed when a force is applied ear canal wall 110 (in cartilaginous region 116). In general, cartilaginous region 116 is much less sensitive to pressure than bony region 118.

In general, application of pressure to ear canal wall 110 (such as by an earplug which occludes ear canal 108), may deform ear canal wall 110. The deformation may, for example, stretch ear canal wall 110 and may place the skin layer under tension. Accordingly, it may be desirable to configure earpiece devices to be inserted within cartilaginous region 116. Earpiece devices may be inserted (and expanded) in cartilaginous region 116 without inducing discomfort and pain.

In general, ear canal 108 may vary substantially in shape and size over the human population. In general, ear canal 108 is not straight or regularly shaped. Although not illustrated in FIG. 1, ear canal 108 typically includes an upward tilt of approximately 45 degrees, such that tympanic membrane 112 is above the opening (i.e., dashed line 106) of ear canal 108. Ear canal 108 typically includes a first bend near the opening to ear canal 108 and a second bend that is proximate to tympanic membrane 112.

Because the volume, shape, and length of ear canal 108 may substantially vary, there has been difficulty in providing a system that may effectively seal ear 100, attenuate noise, mitigate the occlusion effect, operate under different environmental conditions, and may fit a majority of the population. For example, hearing aid manufacturers typically generate a full custom earpiece for individuals that include a mold of the patient's ear canal. The ear canal mold is then used to form a hearing aid housing. The procedure to create an ear canal mold is costly, cumbersome, and is not easily adaptable for high volume production. A earpiece and more particularly an occluding member of the earpiece made of a non-Newtonian fluid can be molded and customized for a particular user's ear canal and most likely by the user themselves by the mere process of insertion of the occluding member into the ear canal.

Figure 2A:
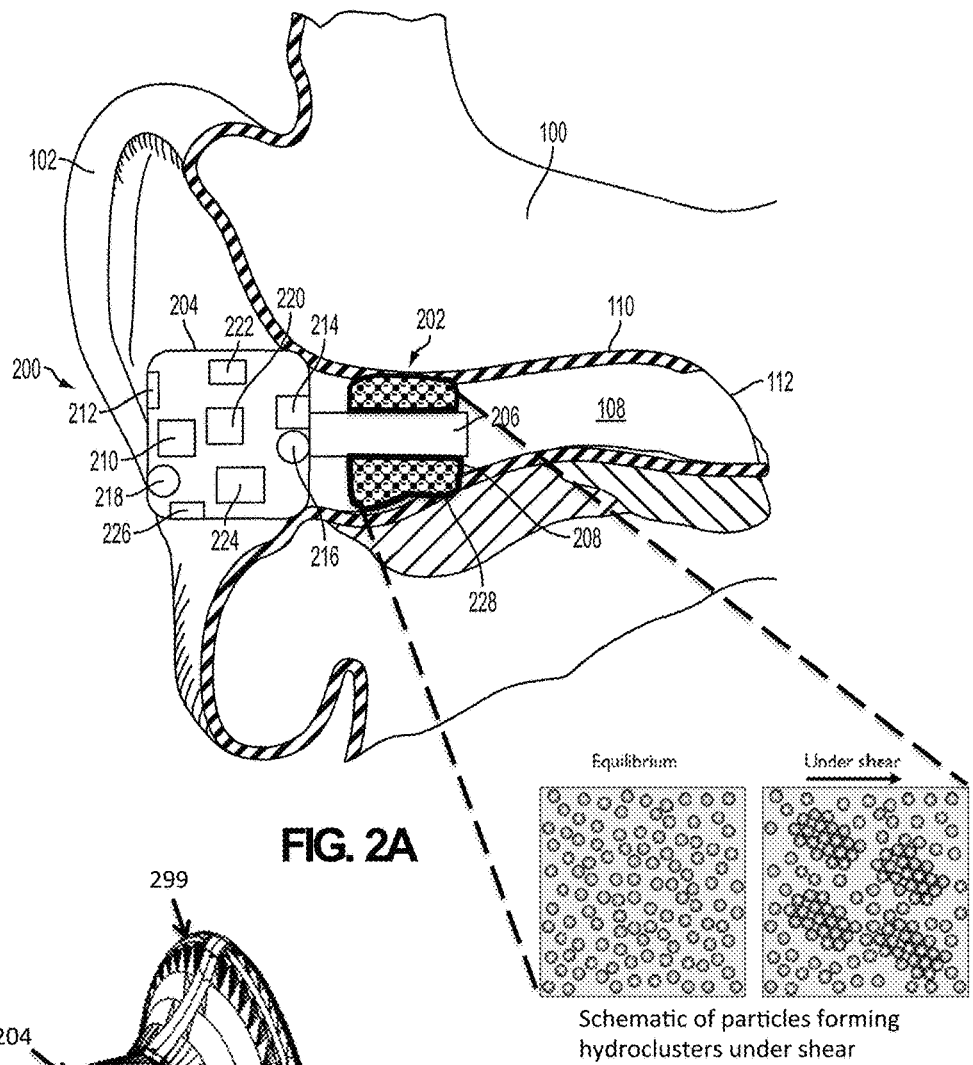
FIG. 2A is a cross section diagram of an exemplary earpiece device inserted in an ear canal, according to an embodiment of the present invention

Referring next to FIG. 2A, a cross section diagram of an exemplary earpiece device 200 is shown. Earpiece device 200 is shown relative to ear 100. Earpiece device 200 may include occlusion member or section 202 and housing unit 204 coupled to occlusion section 202. Occlusion section 202 may be configured to be inserted in ear canal 108, at a location between the entrance to the ear canal 108 and tympanic membrane 112. As discussed above, it may be desirable to position occlusion section 202 within cartilaginous region 116 (FIG. 1) of ear canal 108. Housing unit 204 may be positioned outside of ear canal 108. In FIG. 2A, housing unit 204 is illustrated as being disposed in ear 100. It is understood that housing unit 204 may also be configured to be placed behind ear 100 or may be placed partially behind ear 100 and partially in ear 100.

Occlusion section 202 may include insertion element 206 and expandable element 208. The expandable element 208 can be a balloon containing a non-Newtonian fluid, but alternatively it can be a material that is just a non-Newtonian fluid without the use of a balloon. Insertion element 206 may be coupled to expandable element 208 and may be used to position expandable element 208 in ear canal 108. Expandable element 208 is configured to be expanded or manipulated in shape, via medium 228. Again, the medium 228 can be a non-Newtonian fluid. In general, expandable element 208 may be configured to form an acoustic seal with a portion of ear canal wall 110. Expandable element 208 may be configured to partially or fully occlude ear canal 108, to provide various degrees of acoustic isolation (i.e., attenuation of one or more frequencies of ambient sound) at tympanic membrane 112. Furthermore, with the use of a non-Newtonian fluid, the attenuation characteristic can have increased attenuation as the surface of the element 208 is exposed to greater sound pressure levels (SPL) or volume of sound. In the case of shear thickening fluids, the greater the SPL exposure that the element 208 is exposed to, the greater shear thickening and viscosity the material of element 208 will exhibit. Correspondingly, the greater viscosity will provide greater attenuation characteristics to element 208. As the ambient sound increases, the greater attenuation element 208 will exhibit. As the ambient sound subsides or decreases, the less attenuation element 208 will exhibit. The non-Newtonian essentially operates as a dynamic attenuation device that is passive. In some embodiments, an active component can be added or substituted to provide a user greater control of the attenuation characteristics. For example, if the non-Newtonian fluid comprises electrorheological fluids composed of dispersions of electrically polarizable particles in an insulating fluid, an exposure of the non-Newtonian fluid to an electric field controls the shear viscosity (and hence attenuation characteristics) of the non-Newtonian fluid. Typically a non-Newtonian fluid such as electrorheological fluids increases in shear viscosity when exposed to an electric field. Alternatively, the non-Newtonian fluid can also be magnetorheological fluids composed of dispersions of magnetic particles in an inert or non-magnetic carrier liquid that increases in shear viscosity when exposed to a magnetic field. Thus, controlling the magnetic field about the magnetorheological fluids controls a level of the attenuation characteristic of the element containing the non-Newtonian fluid.

In operation, expandable element 208 may be inserted in ear canal 108 in a contracted state or in a shape that would generally have a smaller diameter than the orifice of the ear canal. After insertion, expandable element 208 may be subsequently expanded (e.g., by being filled with medium 228) or manipulated by squeezing, or pinching, such that expandable element 208 conforms to ear canal 108 and forms at least a partial acoustic seal with ear canal 108. To remove earpiece device 200, expandable element 208 may be manipulated again or contracted (e.g., by removing at least part of medium 228 or manipulating part of the medium towards an external surface) back to the contracted state. Accordingly, earpiece device 200 may then be easily removed from ear canal 108.

Expandable element 208 may be formed from any compliant material that has a low permeability to medium 228. Examples of materials of expandable element 208 include any suitable elastomeric material, such as, without being limited to, silicone, rubber (including synthetic rubber) and polyurethane elastomers (such as PeMethane® and Santoprene™). Materials of expandable element 208 may be used in combination with a barrier layer (for example, a barrier film such as SARANEX™), to reduce the permeability of expandable element 208. In general, expandable element may be formed from any suitable material having a range of Shore A hardness between about 5 A and about 30 A, with an elongation of about 500% or greater.

Medium 228 may include any suitable liquid, gas or gel capable of expanding and contracting expandable element 208 and that would maintain a comfortable level of pressure for a user of earpiece device 200. Examples of medium 228 include, for example, silicone, non or low permeable-based polymers, gels, fully-fluorinated liquids, ethylene glycol, isopropyl alcohol, air or other gasses (for example sulfur hexafluoride (SF6) or hydrogen). In particular embodiments emphasized herein, the medium can include non-Newtonian fluids such as shear thickening fluids and or fluids as described above.

Insertion element 206 may be formed from, for example, thermoplastic elastomer (TPE) materials, materials having an elastomeric property (such as silicone), or other malleable materials capable of conforming to the ear canal. Expandable element 208 may be attached to insertion element 206 via any suitable attachment method, such as, but not limited to, bonding, adherence with an adhesive, thermal bonding, molding and ultrasonic bonding.

Figure 2B:
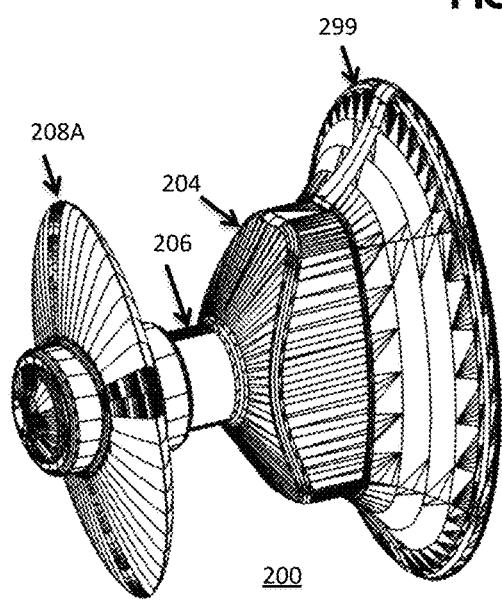
FIG. 2B is a similar earpiece in a different form factor.

Although expandable element 208 is illustrated as being of an annular-disc shape, it is understood that expandable element 208 may be formed of other shapes, such as conical-shaped, or toroidal-shaped. Although FIG. 2A illustrates a single expandable element 208, occlusion section 202 may include multiple co-located expandable elements 208 (such as an inner expandable element in an outer expandable element, where each expandable element 208 may be filled with different mediums 228). Although FIG. 2A illustrates a single expandable element 208, it is understood that occlusion section 202 may include more than one expandable element 208 (for example, as shown in FIG. 8A), where each expandable element 208 may be filled with a same medium 228 or with different mediums 228. As noted previously, the expandable element 208 can include a balloon, but in some embodiments, the non-Newtonian fluid itself can form the element 208 without the use of a balloon or other exterior element. For example, in FIG. 2B, the earpiece 200 can have an occluding member 208A (similar to expandable element 208 of FIG. 2A) that is either made of a non-Newtonian fluid (such as a material like "Silly Putty" described above or non-Newtonian fluids that are capable of being self contained) or comprised of a balloon which has or encloses a medium comprising the non-Newtonian fluid. The earpiece can include a flange 299 that can cover the orifice of the ear but is not intended to completely seal the ear as the balloon is designed for such purpose further into the external auditory canal (EAC). In one embodiment, the flange can also be made of a non-Newtonian fluid. Further note that the embodiments herein are not limited to earpieces, but can include all types of headphones and headsets. In the case of headphones, particularly circum aural headphones that are configured to cover a user's ears can have various portions made of or incorporate non-Newtonian fluids. For example, the foam padding that typically contacts a user's ears can be alternatively made with non-Newtonian fluids or with composites with polyurethane or other alternative materials. The exterior housing of such headphones can also include or be made of non-Newtonian fluids or composites (with microfibers, for example) to provide additional sound attenuation As described further below with respect to FIGS. 5-13, physical parameters of occlusion section 202 may be selected to provide a predetermined sound attenuation characteristic over a frequency band or over ambient SPL levels. For example, a compliance of expandable element 208, the type of medium 228 (such as non-Newtonian fluid), as well as the number of expandable elements 208, may be used to design occlusion section 202 with a specific sound attenuation characteristic (such as a high pass filter or a low pass filter) or a dynamic attenuating filter based on the level of amplitude of an ambient SPL. According to an embodiment of the present invention, an selection of a material for the medium or a selection of particles in a non-Newtonian fluid or other parameters such as an amount of expansion pressure (of medium 228) with which expandable element 208 is expanded may also be selected to control the amount of overall sound attenuation, as well as the amount of occlusion, over the frequency band.

For example, sleep apnea is an example of a noisy environment that can have an impact on the health of the listener. Because snoring typically has a large portion of its power in the lower frequencies in the acoustic range, a listener subjected to snoring could benefit from a high pass filter earpiece that allows higher frequencies of the acoustic signal to be transmitted through the earpiece, while attenuating the lower frequencies. In the case of non-Newtonian fluids, concentration of particles, particle size, and particle shape can all play a roll in configuring and optimizing an occluding element that can attenuate frequencies associated with snoring (or other sources of undesired noise). Other factors that can be used to configure attenuation characteristics can include the specific gravity of the fluid used for the non-Newtonian fluid and the density of the particles, fibers, microparticles or microfibers used for the non-Newtonian fluid. Note that the term "particles" as used herein is intended to be interpreted in a broad sense to include all types of objects that can be used in a non-Newtonian fluid such as spheres, microspheres, fibers, microfibers, or microparticles. In some embodiments, the specific gravity of the fluid is made to match the density of the particles. Furthermore, the location or placement of the non-Newtonian fluid within a device can be varied and the composition of the non-Newtonian fluid can be varied to provide specific attenuation profiles. In other words, the fluid can be customized or designed to have variable compression and decompression or recovery times. As the non-Newtonian fluid hardens or forms clumps under shear forces, the amount of time that the non-Newtonian fluid recuperates or returns to a non-clumped or softened state can also be a factor in its attenuation characteristics. Furthermore, the various variables above can also be selectively manipulated to design a material or composite material that exhibits the shear thickening and attenuation characteristics that begins to manifest at a particular threshold sound pressure level. Non-Newtonian fluids introduces a entire host of additional variables for designing acoustic products (and non-acoustic products that still utilize acoustics in some form) that can benefit from customized attenuation characteristics or parameters not previously available before.

Housing unit 204 may include inflation management system 210 for controlling the transfer of medium 228 to and from occlusion section 202, for expanding and contracting expandable element 208. Housing unit 204 may also include user interface 212 coupled to inflation management system 210. Inflation management system 210 may be activated responsive to user interface 212, in order to expand and contract expandable element 208. Housing unit 204 may also include further electrical components. Inflation management system may include any suitable system capable of transferring medium 228 to and from expandable element 208. For example, inflation management system may include a pump actuator and a valve housing (not shown). In some embodiments, no inflation management system would be used. For example, a system using non-Newtonian fluid can operate by allowing the user to apply pressure to the element 208 itself to manipulate the shape of the element 208 for insertion and removal from the ear canal.

According to one embodiment, earpiece device 200 may include inflation management system 210 and user interface 212, without any electro-acoustic elements. In this example embodiment, earpiece device 200 may be configured simply as a sound isolation device, with a predetermined sound attenuation characteristic selected according to the physical parameters of occlusion section 202. In another embodiment, the, earpiece device 200 may be without an inflation management system 210 as described above.

According to another embodiment, housing unit 204 may include electrical components as well as one or more electro-acoustical components. For example, housing unit 204 may include speaker 214, controller 220, memory 222, battery 224 and communication unit 226.

Speaker 214, memory 222, communication unit 226, user interface 212 and inflation management system 210 may be controlled by controller 220. Controller 220 may include, for example, a logic circuit, a digital signal processor or a microprocessor.

Communication unit 226 may be configured to receive and/or transmit signals to earpiece device 200. Communication unit 226 may be configured for wired and/or wireless communication with an external device (e.g., an MPEG player or a mobile phone).

Battery 224 may power the electrical and electro-acoustic components in housing unit 204. Battery 224 may include a rechargeable or replaceable battery.

The acoustic seal provided by occlusion section 202 may significantly reduce a sound pressure level at tympanic membrane 112 from an ambient sound field at the entrance to ear canal 108 (to provide sound isolation). For example, occlusion section 202 having a high pass filter characteristic may substantially attenuate lower frequencies. Because of the sound isolation of occlusion section 202, speaker 214 may generate a full range bass response time when reproducing sound in earpiece device 200.

According to another embodiment, housing unit 204 may include an ear canal (EC) microphone 216 located adjacent to speaker 214, which may also be acoustically coupled to ear canal 108. EC microphone 216 may be configured to measure a sound pressure level in ear canal 108. The sound pressure level in ear canal 108 may be used, for example, to test the hearing acuity of a user, to confirm an integrity of the acoustic seal, and/or to confirm the operation of EC microphone 216 and speaker 214. Further note that the ear canal microphone can be located in other locations than shown, for example, the ear canal microphone 216 can be located on the other side of the insertion element 206 residing well within the ear canal in some embodiments. The wiring for the ear canal microphone 216 in such instance can be fed through the insertion element 206 which can be a tube or channel that goes through the element 208.

According to another embodiment, housing unit 204 may include ambient microphone 218, as well as EC microphone 216 and speaker 214. Ambient microphone 218 may be configured to monitor a sound pressure of the ambient environment at the entrance to ear 100. In at least one exemplary embodiment, earpiece device 200 may actively monitor a sound pressure level both inside and outside ear canal 108 and may enhance spatial and timbral sound quality, while maintaining supervision to ensure safe sound reproduction levels. Earpiece device 200, in various embodiments may conduct listening tests, filter sounds in the environment, monitor sounds in the environment, present notification based on the monitored sounds, maintain constant audio content to ambient sound levels, and/or filter sound in accordance with a personalized hearing level.

Earpiece device 200 may be configured to generate an ear canal transfer function (ECTF) to model ear canal 108 (via speaker 214 and EC microphone 216), as well as an outer ear canal transfer function (OETF) (via ambient microphone 218). Earpiece device 200 may be configured to determine a sealing profile with ear 100 to compensate for any acoustic leakage. Earpiece device 200 may be configured to monitor a sound exposure to ear canal 108 (for example, from speaker 214 as well as from ambient noise measured via ambient microphone 218).

Figure 3:
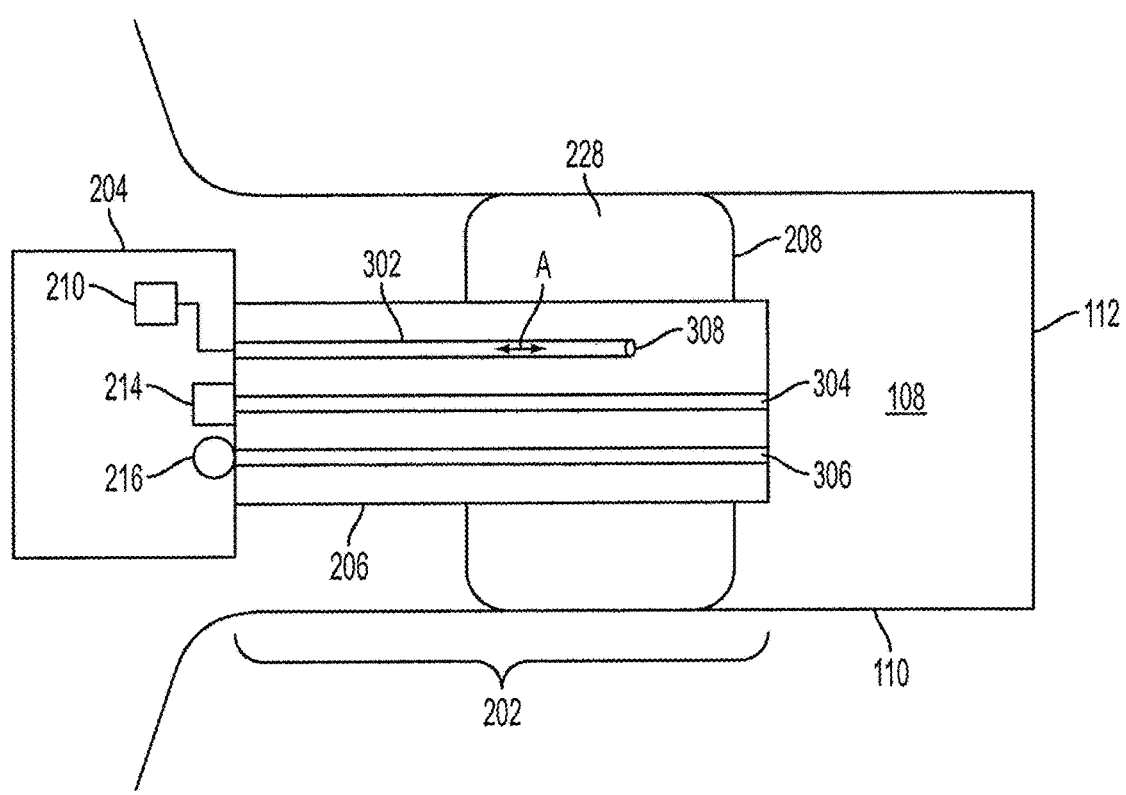
FIG. 3 is a cross section diagram of a portion of the earpiece device shown in FIG. 2, according to an embodiment of the present invention.

Referring to FIG. 3, a cross section diagram of earpiece device 200 is shown, which illustrates further components of insertion element 206. In FIG. 3, only some of the components of housing unit 204 are shown, for convenience. According to an exemplary embodiment, insertion element 206 may include pneumatic channel 302. Pneumatic channel 302 may be coupled to expandable element 208 and to inflation management system 210. Pneumatic channel 302 may be used to transfer medium 228 (illustrated by double headed arrow A) to and from expandable element 208 via port 308.

In at least one exemplary embodiment, insertion element 206 may include at least one acoustic channel (e.g., acoustic channel 304 and/or acoustic channel 306) for receiving or delivering audio content. For example, housing unit 204 may include speaker 214. Insertion element 206 may, thus, include acoustic channel 304 for delivering sound from speaker 214 to ear canal 108. As another example, housing unit 204 may include speaker 214 and EC microphone 216. In this example, insertion element 206 may include acoustic channels 304, 306, respectively coupled to speaker 214 and EC microphone 216. Acoustic channel 306 may deliver sound from ear canal 108 to EC microphone 216.

As described above, expandable element 208 may form an acoustic seal with ear canal wall 110 at a location between the entrance (the orifice) to ear canal 108 and tympanic membrane 112. The acoustic seal by expandable element 208 may substantially attenuate sound in ear canal 108 from the ambient environment (thus providing sound isolation to ear canal 108). Insertion element 206 may also include one or more acoustic channels (e.g., acoustic channel 304 and/or acoustic channel 306) for acoustically coupling sound between ear canal 108 and one or more respective transducers (e.g., speaker 214 and/or EC microphone 216). Accordingly, sound transmitted to and/or from ear canal 108 via acoustic channel 304 (and/or 306) may be substantially isolated from the ambient environment.

Figure 4A:
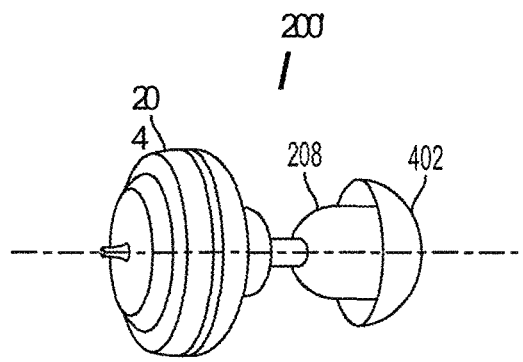
FIGS. 4A and 4B are respective perspective view and cross section diagrams of an exemplary earpiece device in an expanded state, according to another embodiment of the present invention.
Figure 4C:
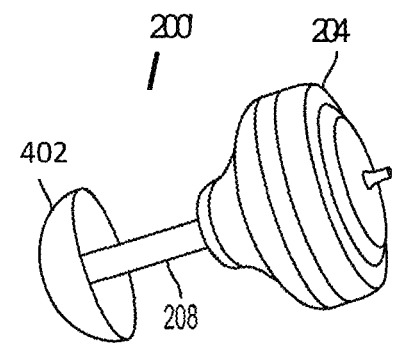
FIGS. 4C and 4D are respective perspective view and cross section diagrams of the earpiece device shown in FIGS. 4A and 4B in a contracted state.
Figure 4B:
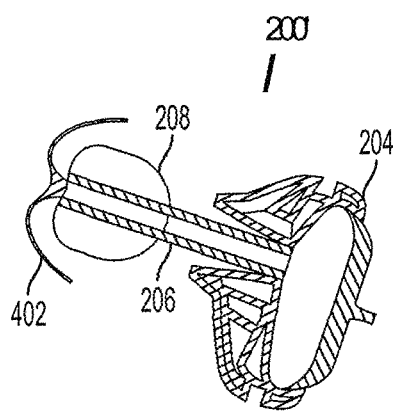
Figure 4D:
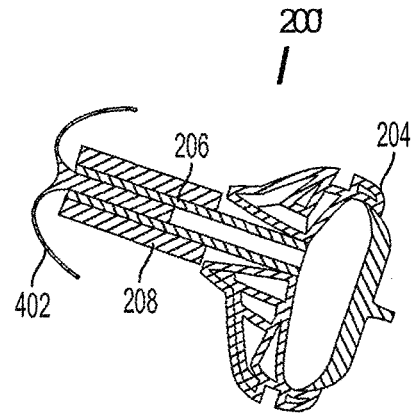

Referring next to FIGS. 4A-4D, exemplary earpiece device 200' is shown. In particular, FIG. 4A is a perspective view diagram of earpiece device 200' with expandable element 208 in an expanded state; FIG. 4B is a cross section diagram of earpiece device 200' with expandable element 208 in the expanded state: FIG. 4C is a perspective view diagram of earpiece device 200' with expandable element 208 in a contracted state; and FIG. 4D is a cross-section diagram of earpiece device 200' with expandable element 208 in the contracted state.

Earpiece device 200' is similar to earpiece device 200 except that earpiece device 200' includes flange 402 coupled to insertion element 206 of occlusion section 202. Flange 402 may provide sound attenuation (in addition to the sound attenuation by expandable element 208). Flange 402 may also help to seat occlusion section 202 in ear canal 108 (FIG. 2). Flange 402 may be formed of materials similar to expandable element 208.

The selection of physical parameters of occlusion section 202 (FIG. 2) to provide predetermined sound attenuation characteristics is described below.

It is often possible and convenient to represent an acoustical system with a lumped element model, as an acoustical circuit analogous to an electrical circuit. For example, an acoustical system may be represented as an acoustic impedance (or acoustic mobility). In acoustic impedance analogs, for example, the sound pressure and volume velocity correspond to voltage and current, respectively. For example, occlusion section 202 (FIG. 2) in ear canal 108 may be modeled by an acoustical impedance circuit.

Figure 5A:
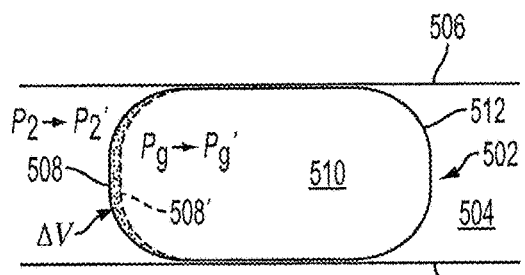
FIG. 5A is a cross section diagram of an exemplary expandable element in a tube illustrating a change in static pressure, according to an embodiment of the present invention.
Figure 5B:
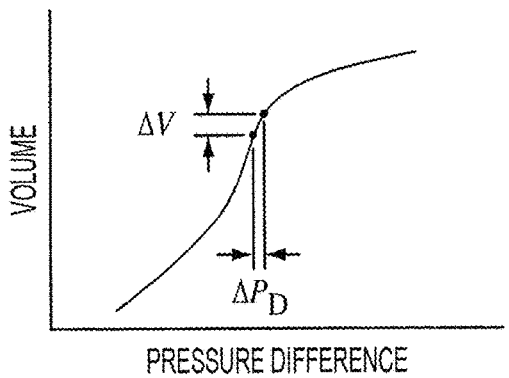
FIG. 5B is graph of volume as a function of pressure difference for the expandable element shown in FIG. 5A.

Referring to FIGS. 5A and 5B, an equivalent acoustical element representation of balloon 502 (an example of an expandable element) filled with medium 510 in tube 504 is described. In particular, FIG. 5A is a cross section diagram of balloon 502 in tube 504; and FIG. 5B is an example of a volume of one face of balloon 502 (for example, face 508) with pressure difference.

Balloon 502 and medium 510 may each be represented as acoustical elements. Because balloon 502 is within tube 504, the band of balloon material in contact with tube walls 506 does not move. This effectively separates balloon 502 into two parts, upstream face 508 and downstream face 512. It is understood that the acoustical element representation of downstream face 512 is the same as that of upstream face 508. Thus, only upstream face 508 is considered below.

Face 508 of balloon 502 (filled with medium 510) includes a static DC pressure $P_2$ on the outside and a static interior pressure $P_g$. If the outside pressure is changed to $P_2'$, there will be a change in the static equilibrium of the balloon. Face 508 moves to a new position and may have a different shape (represented as face 508'), sweeping out a volume $\Delta V$. Thus, the interior pressure will change to a new value $P_g'$. The shape of the balloon face 508 is controlled by the difference in pressure across the material, i.e., $P_D = P_2 - P_g$ and $P_D' = P_2' - P_g'$.

Although, in general, the relationship between the change in pressures and the volume of balloon 502 may be complicated, for the acoustical behavior, it is assumed that these changes are very small, so that a simple acoustical representation of balloon 502 may be determined.

FIG. 5B illustrates an example of the volume change of face 508 of balloon 502 with a change in pressure difference across the material. Over a small change in pressure difference $\Delta P_D$, the curve is very nearly linear and the volume change $\Delta V$ may be represented as:

$$\Delta V \approx \left(\frac{\partial V}{\partial P_D}\right)_{P_D} \Delta P_D \equiv C_2\, \Delta P_D. \quad (1)$$

For acoustic pressures, the pressures acting on face 508 may be considered to oscillate sinusoidally in time about their static values, and may be represented by complex notation as $$P_2' = P_2 + Re\{p_2\, e^{i\omega t}\} \quad (2)$$

$$P_g' = P_g + Re\{p_g\, e^{i\omega t}\} \quad (3)$$

where $p_g$ and $p_2$ are the (complex) sound pressures on either side of the balloon section, so that $$\Delta P_D = Re\{(p_2 - p_g)e^{i\omega t}\}. \quad (4)$$

Similarly, the volume changes harmonically as $$\Delta V = V' - V = Re\{V^*\, e^{i\omega t}\} \quad (5)$$

where V is the static volume enclosed by face 508 of the balloon. Thus, the volume velocity U (i.e., the rate change of volume with time) may be represented as $$U \equiv Re\{u_2 e^{i\omega t}\} = \frac{dV'}{dt} = Re\{i\omega V^* e^{i\omega t}\}. \quad (6)$$

Accordingly, the sound pressure difference is related to the complex volume velocity $u_2$, as $$p_2 - p_g = \frac{u_2}{i\omega C_2} \quad (7)$$

where $C_2$ is the acoustical capacitance of one side (for example face 508) of balloon 502. The value of capacitance $C_2$ may be determined by the slope of the tangent line in FIG. 5B.

Medium 510 may include, for example, a gas or a liquid. The acoustical element representation of medium 510 may be different depending on whether medium 510 is a gas or a liquid. The consideration of medium 510 as a liquid is discussed with respect to FIG. 12. The acoustical representation of medium 510 that includes a gas is considered below. Accordingly, medium 510 is referred to below as gas 510.

An enclosed volume of gas may store energy in its compressions. Thus, gas 510 (for example, air) within balloon 502 may also be represented as an acoustic capacitance. The volume velocity $u_2$, as defined, acts to compress gas 510 contained within balloon 502. The volume velocity corresponding to face 512 of balloon 502 may be defined in the opposite sense, such that the volume velocity $u_1$ acts to uncompress the air. The net volume velocity $(u_2 - u_1)$ is related to the sound pressure $p_g$ inside the balloon by:

$$u_{2-1} = i\omega C_g p_g \quad (8)$$

where capacitance $C_g$ is given by:

$$C_g = \frac{V_g}{\gamma P_g} \quad (9)$$

and where $V_g$ is the enclosed volume, $P_g$ is the static pressure inside balloon 502, and $\gamma$ is the specific heat ratio.

Figure 6A:
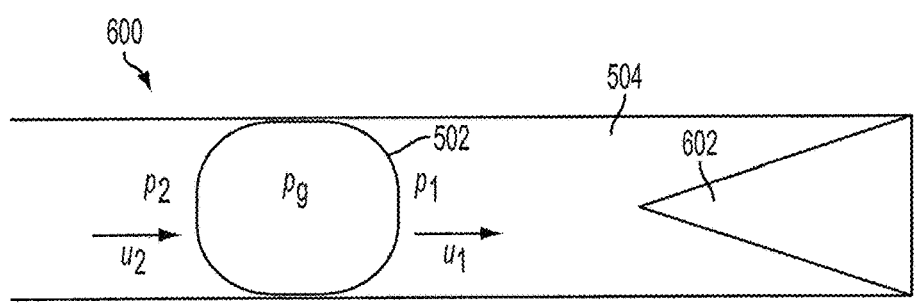
FIG. 6A is a cross section diagram of an exemplary acoustical system, according to an embodiment of the present invention
Figure 6B:
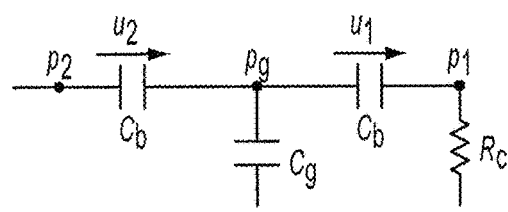
FIG. 6B is an electro-acoustical circuit diagram representing the acoustical system shown in FIG. 6A, according to an embodiment of the present invention.

Referring to FIGS. 6A and 6B, acoustical system 600 representing an expandable element in an ear canal is shown. In particular, FIG. 6A is a cross section diagram of acoustical system 600 including balloon 502 in tube 504 having anechoic termination 602; and FIG. 6B is an electro-acoustical circuit diagram of acoustical system 600. Acoustical system 600 represents an expandable element (balloon 502) in an ear canal (tube 504) having a tympanic membrane (anechoic termination 602). Although not illustrated, balloon 502 may be formed on an insertion element (such as insertion element 206 shown in FIG. 2).

If the lateral dimensions of tube 504 are less than a wavelength of sound, sound waves may propagate along both forward and backward longitudinal directions. Because tube 504 includes anechoic termination 602, there are no reflected sound waves, only forward propagating waves.

Consider pressure $p_1$ and volume velocity $u_1$ at a position in tube 504. For a plane wave traveling in a single direction, the pressure and the volume velocity are in phase and are related as:

$$p_1 = R_c u_1 \quad (10)$$

where the characteristic acoustical resistance of tube 504 (at anechoic termination 602) is $$R_c = \frac{\rho c}{A}. \quad (11)$$

Here, A is the internal cross-sectional area of tube 504, $\rho$ is the density of the gas (e.g., air), and c is the sound speed in the gas (e.g., air).

As discussed above, faces 508, 512 of balloon 502 may each be represented as acoustical compliance $C_b$. Gas 510 within balloon 502 may be represented as acoustical compliance $C_g$. Finally, tube 504 with anechoic termination 602 may be represented as resistance $R_c$.

Based on the acoustical elements representing balloon 502, gas 510 and tube 504, acoustical system 600 may be represented as an equivalent electro-acoustical circuit (i.e., an acoustical impedance analog), as shown in FIG. 6B. Thus capacitance $C_b$ of face 508 receives pressure $p_2$. Capacitance $C_b$ is coupled to capacitance $C_g$ of gas 510 and capacitance $C_b$ of face 512. Capacitance $C_b$ of face 512 is coupled to resistance $R_c$ of the termination of tube 504. Thus, pressure $p_2$ is provided at an output terminal of the circuit. It is understood that the electro-acoustic circuit may be modified to account for the finite size of insertion element 206 (FIG. 2) on which balloon 502 may be mounted.

Network methods may be applied to calculate the various quantities of the acoustical elements if values for the various circuit elements are available. Both $R_c$ and $C_b$ may be determined from the expressions provided above.

For a sample calculation, it is assumed that tube 504 has an inner diameter of 9.53 mm (0.375") and that balloon 502 contains a volume of 0.713 cm$^3$ at an inflation pressure of 300 mbar. Capacitance $C_b$ corresponding to each face of balloon 502 may be determined, for example, based on a calculation of the inflation dynamics of balloon materials, taking into account the Mooney-Rivlin type of stress-strain relationship. In the sample calculation, several different values of capacitance including $C_b = 0.3\ C_g$, $C_b = C_g$, and $C_b = 3\ C_g$ are selected. The transmission coefficient of acoustical energy may be determined as:

$$T = 20 \log \left| \frac{p_1}{p_2} \right|. \tag{12}$$

Figure 7:
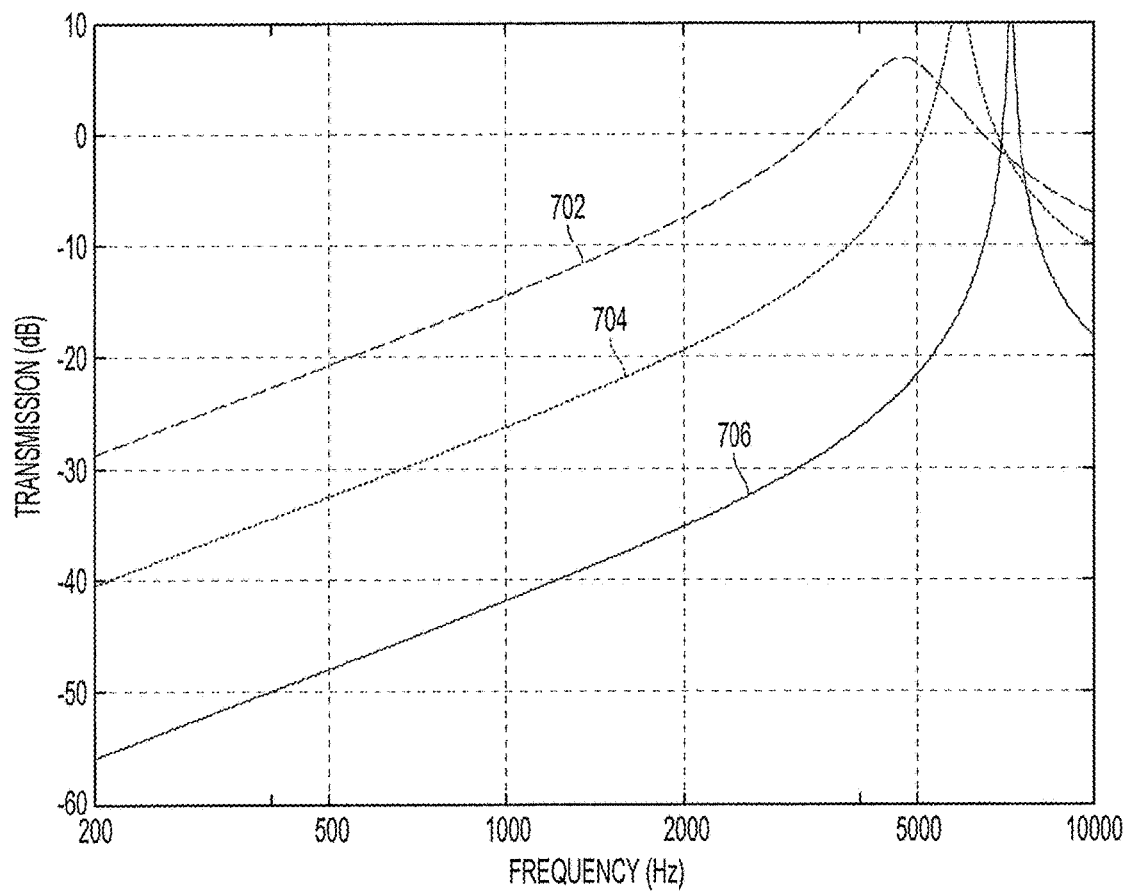
FIG. 7 is a graph of transmission as a function of frequency for the electro-acoustic circuit diagram shown in FIG. 6B, for various capacitance values of an expandable element.
Figure 8A:
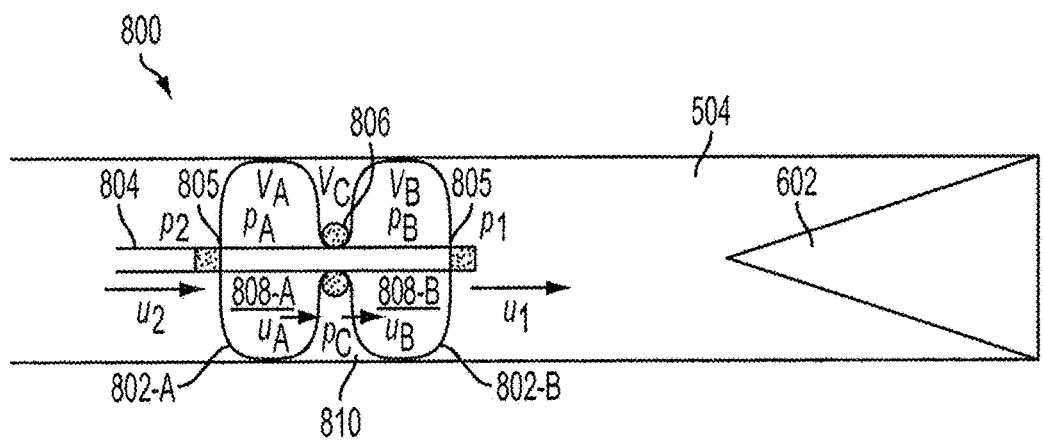
FIG. 8A is a cross section diagram of an exemplary acoustical system, according to another embodiment of the present invention

Referring to FIG. 7, the calculated transmission coefficients for these three values of capacitance $C_b$ are shown. Curves 702, 704 and 706 represent capacitance values $C_b=3 C_g$, $C_b=C_g$ and $C_b=0.3\ C_g$, respectively. All curves show about a 6 decibel (dB) per octave drop off at the lower frequencies. Accordingly, balloon 502 acts as a first order high-pass filter.

Figure 8B:
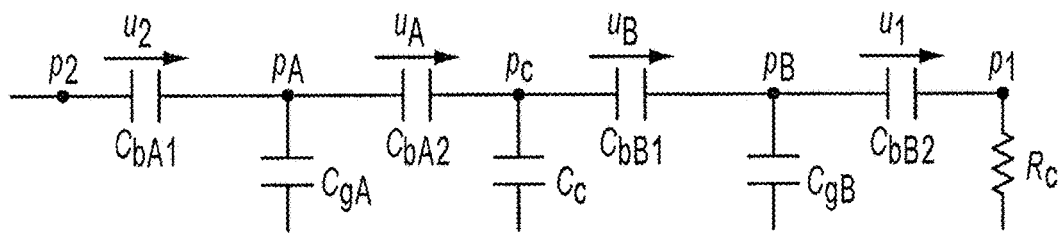
FIG. 8B is an electro-acoustical circuit diagram representing the acoustical system shown in FIG. 8A, according to an embodiment of the present invention.

Referring next to FIGS. 8A and 8B, acoustical system 800 is shown, which represents two expandable elements in an ear canal. In particular, FIG. 8A is a cross section diagram of acoustical system 800 including balloons 802-A, 802-B in tube 504 having anechoic termination 602; and FIG. 8B is an electro-acoustical circuit diagram of acoustical system 800. Balloons 802-A, 802-B are filled with gas 808-A, 808-B.

Acoustical system 800 is similar to acoustical system 600 (FIGS. 6A and 6B), except that acoustical system 800 includes two balloons 802-A, 802-B (i.e., two expandable elements), and balloons 802-A, 802-B are illustrated as being mounted on insertion element 804. Two balloons 802-A, 802-B may be formed, for example, from a single balloon material attached to insertion element 804 at attachment points 805 and 806. In an exemplary embodiment, attachment point 806 represents an O-ring approximately midway along a length of a single balloon. As another example, balloons 802-A, 802-B may be formed from different balloon materials attached at respective attachment points 805, 806. Gas 808-B may be the same as gas 808-A or may be different from gas 808-A.

Balloons 802-A, 802-B have respective volumes of $V_A$ and $V_B$, with respective sound pressures of $p_A$ and $p_B$. Gap 810 between balloons 802-A, 802-B (at attachment point 806) has volume $V_C$ and sound pressure $p_C$. The motion of the right-hand face of balloon 802-A includes a volume velocity $u_A$. Similarly, the motion of the left-hand face of balloon 802-B includes a volume velocity $u_B$.

Based on the acoustical elements described above for balloon 502 (FIGS. 6A and 6B), gas 510 and tube 504, acoustical system 800 may also be represented as an equivalent electro-acoustical circuit (i.e., an acoustical impedance analog), as shown in FIG. 8B. Thus, capacitances $C_{bA1}$, $C_{gA}$, $C_{bA2}$ are associated with the left face of balloon 802-A, gas 808-A and the right face of balloon 802-A, respectively. Capacitance $C_C$ is associated with gap 810. Capacitances $C_{bB1}$, $C_{gB}$, $C_{bB2}$ are associated with the left face of balloon 802-B, gas 808-B and the right face of balloon 802-B, respectively. Although not shown, it is understood that the electro-acoustic circuit shown in FIG. 8B may be modified to account for insertion element 804.

Figure 9:
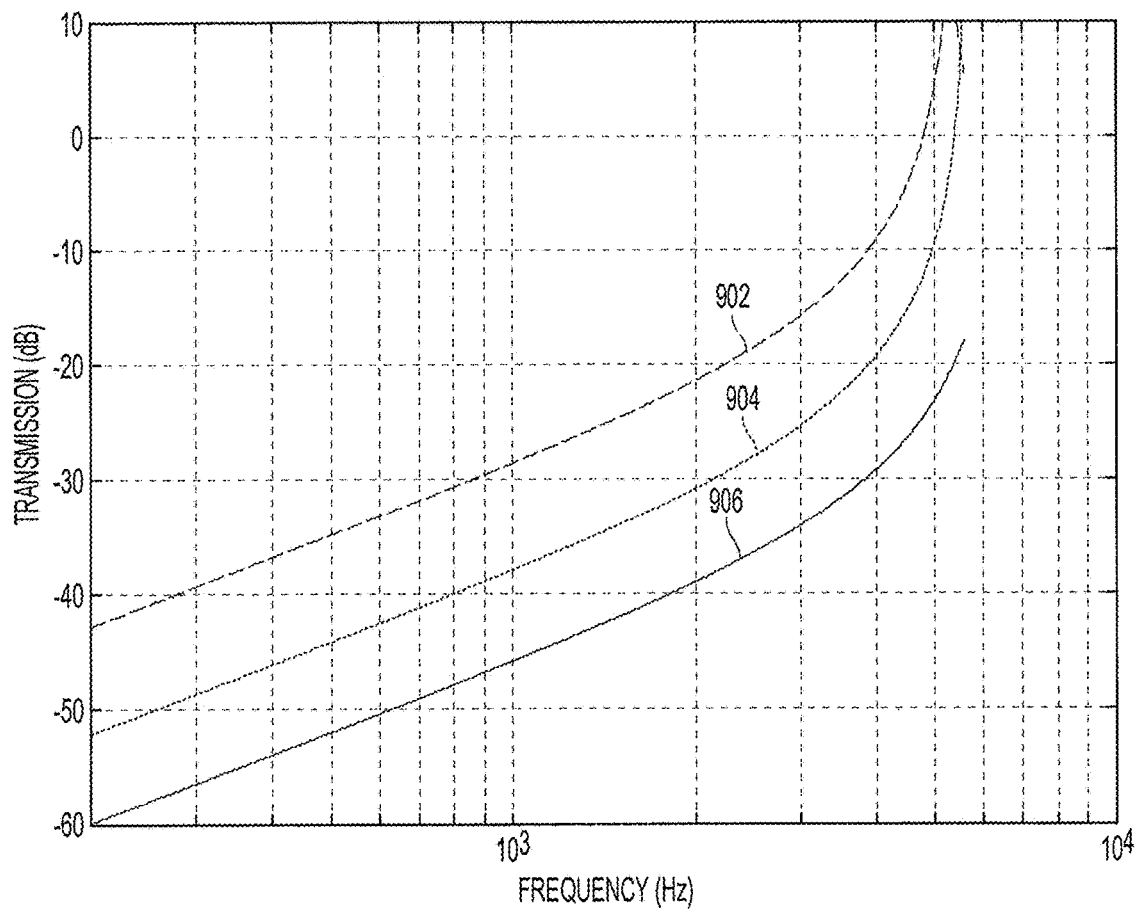
FIG. 9 is a graph of transmission as a function of frequency for the electro-acoustic circuit diagram shown in FIG. 8B, for various capacitance values of expandable elements.

Referring to FIG. 9, example transmission coefficients are shown for the electro-acoustic circuit shown in FIG. 8B, using several different values of capacitance. In this example, both balloons 802-A, 802-B have a volume of 0.222 cm³ and an inflation pressure of 300 mbar, so that $C_{gA}=C_{gB}$. Gap 810 between balloons 802-A, 802-B is at atmospheric pressure and has a volume of 0.095 cm³. Three different selections of balloon capacitances are used. For curve 902, the capacitances are $C_{bA1}=C_{bA2}=C_{bB1}=C_{bB2}=3C_{gA}$. For curve 904, the capacitances are $C_{bA1}=C_{bB1}=3C_{gA}$ and $C_{bA2}=C_{bB2}=C_{gA}$. For curve 904, the capacitances are $C_{bA1}=C_{bA2}=C_{bB1}=C_{bB2}=C_{gA}$.

As shown in FIG. 9, the acoustical transmission for two balloons 802-A, 802-B is similar to the acoustical transmission of a single balloon (shown in FIG. 7). Thus, similar to the single balloon (FIG. 7), the combination of two balloons 802-A, 802-B also acts like a first-order high-pass filter, with approximately a 6 dB/octave slope at low frequencies.

FIG. 8A illustrates acoustical system 800 including two balloons 802-A, 802-B disposed along a length of insertion element 804 (i.e., in series arrangement, as illustrated in FIG. 8B). According to another embodiment, balloons 802-A, 802-B may be co-located on insertion element 804. Balloons 802-A, 802-B, thus, may be formed in a parallel arrangement.

Measurements on several double balloons, however, have revealed a more complicated variation with frequency. This variation may be due to small leaks between balloons 802-A, 802-B.

Figure 10A:
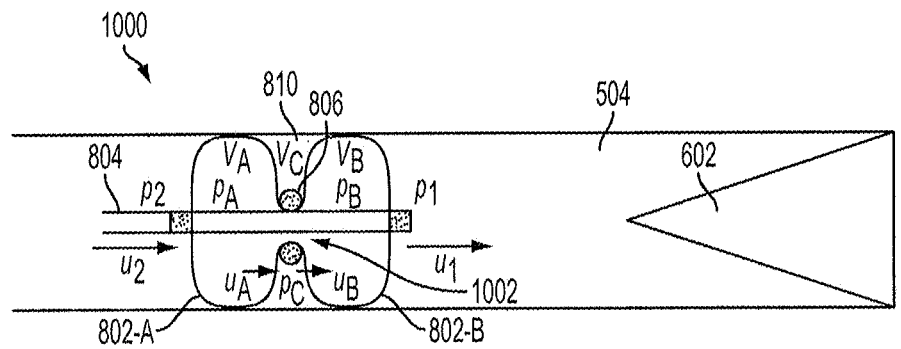
FIG. 10A is a cross section diagram of an exemplary acoustical system, according to another embodiment of the present invention
Figure 10B:
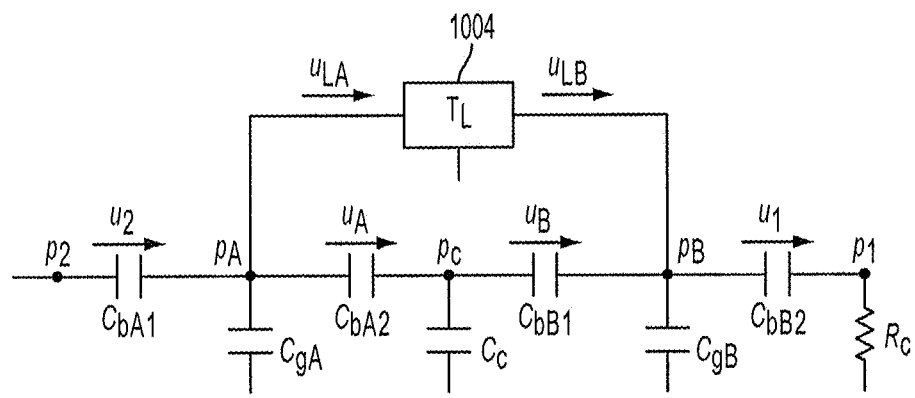
FIG. 10B is an electro-acoustical circuit diagram representing the acoustical system shown in FIG. 10A, according to an embodiment of the present invention

Referring next to FIGS. 10A and 10B, acoustical system 1000 is shown, which represents two expandable elements in an ear canal. In particular, FIG. 10A is a cross section diagram of acoustical system 1000 including balloons 802-A, 802-B in tube 504 having anechoic termination 602; and FIG. 10B is an electro-acoustical circuit diagram of acoustical system 1000. Acoustical system 1000 is similar to acoustical system 800 (FIGS. 8A and 8B), except that acoustical system 1000 includes leak 1002 at attachment point 806.

Leak 1002 may be modeled as a short, circular passage between balloons 802-A, 802-B. The volume velocity entering leak 1002 is represented as $u_{LA}$ and the volume velocity exiting leak 1002 is represented as $u_{LB}$. A volume of fluid (gas or liquid) that has a length comparable or greater than a wavelength (or a radius that is comparable or smaller than a viscous boundary layer thickness) may not be capable of being treated as a simple volume. Accordingly, a general theory is described below for acoustical propagation along a circular passage (i.e., leak 1002).

Consider that leak 1002 is a hollow, circular passage of radius $a_L$ and length l. At one end of leak 1002, there is a pressure $p_A$ and volume velocity $u_{LA}$; at the other end, there is a pressure $p_B$ and volume velocity $u_{LB}$. These quantities are related, generally, through a transfer matrix $T_L$ as:

$$\begin{bmatrix} p_A \\ u_{LA} \end{bmatrix} = T_L \begin{bmatrix} p_B \\ u_{LB} \end{bmatrix} = \begin{bmatrix} \cosh \Gamma \ell & Z \sinh \Gamma \ell \\ Z^{-1} \sinh \Gamma \ell & \cosh \Gamma \ell \end{bmatrix} \begin{bmatrix} p_B \\ u_{LB} \end{bmatrix} \tag{13}$$

where $$\Gamma = i \frac{\omega}{c} \sqrt{\frac{T_\alpha}{T_\beta}} \tag{14}$$

$$Z = \frac{\rho c}{\pi a_L^2 \sqrt{T_\alpha T_\beta}} \tag{15}$$

with $$T_\alpha = 1 + \frac{2(\gamma - 1)J_1(a_L \alpha)}{a_L \alpha J_0(a_L \alpha)} \tag{16}$$

$$T_\beta = 1 - \frac{2 J_1(a_L \beta)}{a_L \beta J_0(a_L \beta)} \tag{17}$$

$$\alpha = \sqrt{\frac{-i \rho \omega N_{pr}}{\mu}} \tag{18}$$

$$\beta = \sqrt{\frac{-i \rho \omega}{\mu}} \tag{19}$$

where µ represents the coefficient of viscosity of the gas (e.g., air), γ represents the ratio of specific heats, $N_{pr}$ represents the Prandtl number and $J_0(*), J_1(*)$ represent Bessel functions of the first kind for respective integer orders 0 and 1.

Leak 1002 that is a circular tube, in general, does not have a simple lumped-element representation. However, leak 1002 may be represented as a network block in an electro acoustical circuit. Accordingly, based on the acoustical elements described above, acoustical system 1000 having leak 1002 may also be represented as an equivalent electro-acoustical circuit (i.e., an acoustical impedance analog), as shown in FIG. 10B. In FIG. 10B, network block 1004 with transfer matrix $T_L$ represents leak 1002. The circuit shown in FIG. 10B is similar to the circuit shown in FIG. 8B, except for the inclusion of network block 1004. Network block 1004 may act in parallel to some of the circuit elements representing balloons 802-A, 802-B.

Figure 11:
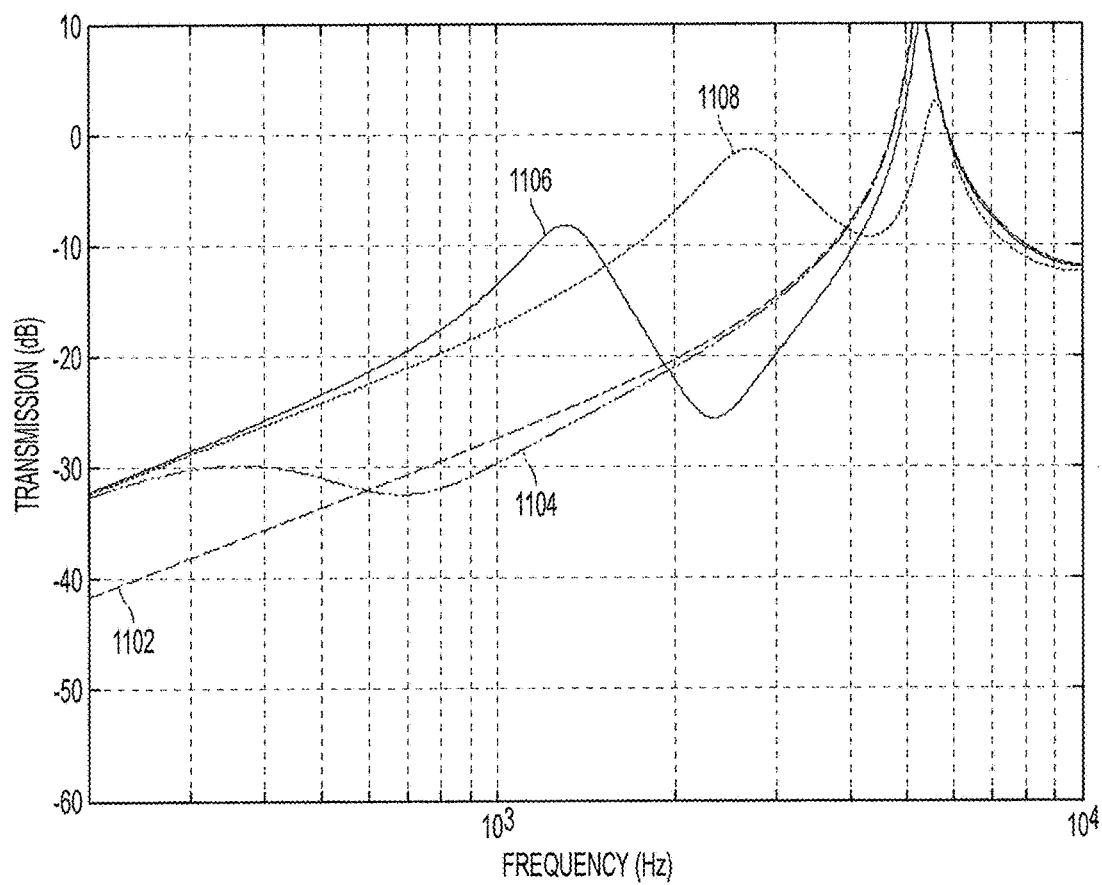
FIG. 11 is a graph of transmission as a function of frequency for the electro-acoustic circuit diagram shown in FIG. 10B, for various leak sizes between expandable elements.

Referring to FIG. 11, example transmission coefficients are shown for the electro-acoustical circuit shown in FIG. 10B, using several different leak sizes (and eq. (13) for the transfer matrix $T_L$). The leak sizes include radii of 0 cm (i.e., no leak), 0.017 cm, 0.05 cm and 0.1 cm. In particular, curves 1102, 1104, 1106 and 1108 represent respective leak sizes of 0 cm, 0.017 cm, 0.05 cm, and 0.1 cm. As shown in FIG. 11, there is a transition from one type of behavior to another with leak size. For a large radius leak (curve 1108), acoustical system 1000 effectively represents a single large balloon, with a 6 dB/octave drop at low frequencies. For a zero leak (curve 1102), acoustical system 1000 represents a double balloon system, also with a 6 dB/octave low frequency behavior. At intermediate sized leaks (curves 1104 and 1106), acoustical system 1000 transitions from a single balloon mode at low frequencies to a double balloon mode at high frequencies, thus producing a more complex frequency variation over approximately the 200 Hz-2000 Hz range. In the example shown in FIG. 11, the attenuation is relatively flat for the 0.017 cm leak (curve 1104). Accordingly, it may be possible to design leaks between balloons 802-A, 802-B to selectively shape the transmission (and attenuation) to a desired response over a range of frequencies.

Figure 12A:
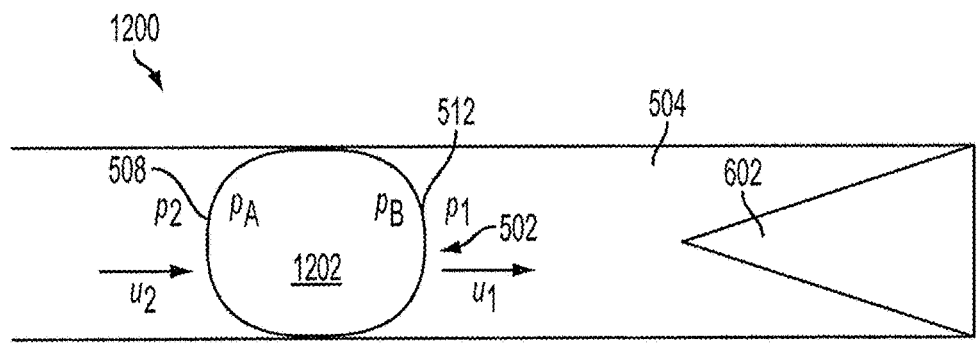
FIG. 12A is a cross section diagram of an exemplary acoustical system, according to another embodiment of the present invention.
Figure 12B:
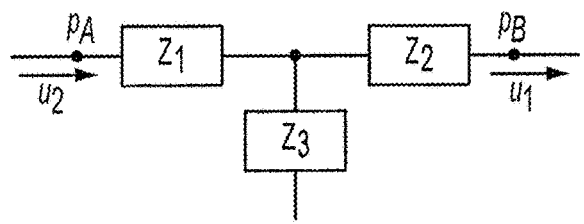
FIG. 12B is a circuit diagram of a transfer network associated with the acoustical system shown in FIG. 12A.
Figure 12C:
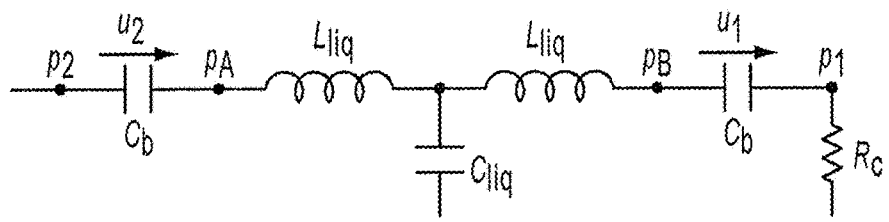
FIG. 12C is an electro-acoustical circuit diagram representing the acoustical system shown in FIG. 12A, according to an embodiment of the present invention.

Referring next to FIGS. 12A-12C, acoustical system 1200 is shown, which represents a liquid-filled expandable element in an ear canal. In particular, FIG. 12A is a cross section diagram of acoustical system 1200 including balloon 502 filled with liquid 1202 in tube 504 having anechoic termination 602; FIG. 12B is a circuit diagram of a transfer network associated with balloon 502 filled with liquid 1202; and FIG. 12C is an electro-acoustical circuit diagram of acoustical system 1200.

Acoustical system 1200 is similar to acoustical system 600 (FIGS. 6A and 6B), except that acoustical system 1200 includes balloon 502 filled with liquid 1202. Filling balloon 502 with liquid 1202 (for example, water instead of air), may change the acoustical behavior of balloon 502. If balloon 502 is of sufficiently short length, it may be treated as a small volume (similar to holding a volume of gas as described above). For balloon 502 having a length comparable to a wavelength, balloon 502 may be treated as a transmission line. This may be the case for liquid 1202, because the sound speed in liquids is considerably higher than in air, such that the wavelengths are correspondingly longer. In the case of non-Newtonian liquids, the sound speeds may vary from conventional liquids.

The pressure just inside face 508 of balloon 502 is represented as $p_A$ and the pressure just inside face 512 is represented as $p_B$. Let L be the length of the balloon and a, the internal diameter of the constraining tube. The sound pressures ($p_A, p_B$) and volume velocities ($u_1, u_2$) may be related through a transfer matrix $T_{liq}$ by:

$$\begin{bmatrix} p_A \\ u_2 \end{bmatrix} = T_{liq} \begin{bmatrix} p_B \\ u_1 \end{bmatrix} = \begin{bmatrix} \cosh \Gamma L & Z \sinh \Gamma L \\ Z^{-1} \sinh \Gamma L & \cosh \Gamma L \end{bmatrix} \begin{bmatrix} p_B \\ u_1 \end{bmatrix} \quad (20)$$

If a is sufficiently large, viscous and thermal boundary layer effects may be ignored, such that the arguments aα and aβ are also large and $T_\alpha \approx T_\beta \approx 1$. Then, $$\begin{bmatrix} p_A \\ u_2 \end{bmatrix} \approx \begin{bmatrix} \cos kL & iZ_{liq} \sin kL \\ iZ_{liq}^{-1} \sin kL & \cos kL \end{bmatrix} \begin{bmatrix} p_B \\ u_1 \end{bmatrix} \quad (21)$$

where $k=\omega/c_{liq}$ is the wavenumber and $Z_{liq}$ is the characteristic impedance of the liquid, given as $$Z_{liq} = \frac{\rho_{liq} c_{liq}}{\pi a^2}. \quad (22)$$

As shown in FIG. 12B, eq. (21) may be represented as a transfer network. For the transfer network:

$$Z_1 = Z_2 = Z_3(\cos kL - 1) \quad (23)$$

where $$Z_3 = \frac{Z_{liq}}{i \sin kL}. \quad (24)$$

If it is further assumed that kL is small, the expressions simplify further, yielding $$Z_1 = Z_2 = i\omega L_{liq} \quad (25)$$

where $$Z_3 = \frac{1}{i\omega C_{liq}}. \quad (26)$$

In eqs. (25) and (26), $L_{liq}$ represents an inductance and $C_{liq}$ represents a capacitance, respectively, where:

$$L_{liq} = \frac{\rho_{liq} L}{\pi a^2} \quad (27)$$

and $$C_{liq} = \frac{\pi a^2 L}{\rho_{liq} c_{liq}^2}. \quad (28)$$

The inductance $L_{liq}$ is directly related to the mass of the liquid contained in the volume. The capacitance $C_{liq}$ is related to the compliance of the liquid.

Accordingly, based on the acoustical elements described above, and the transfer network shown in FIG. 12B, acoustical system 1200 may be represented as an equivalent electro-acoustical circuit (i.e., an acoustical impedance analog), as shown in FIG. 12C. The circuit shown in FIG. 12C is similar to the circuit shown in FIG. 6B, except for the inclusion of inductances $L_{liq}$, and the replacement of capacitance $C_g$ with capacitance $C_{liq}$.

Figure 13:
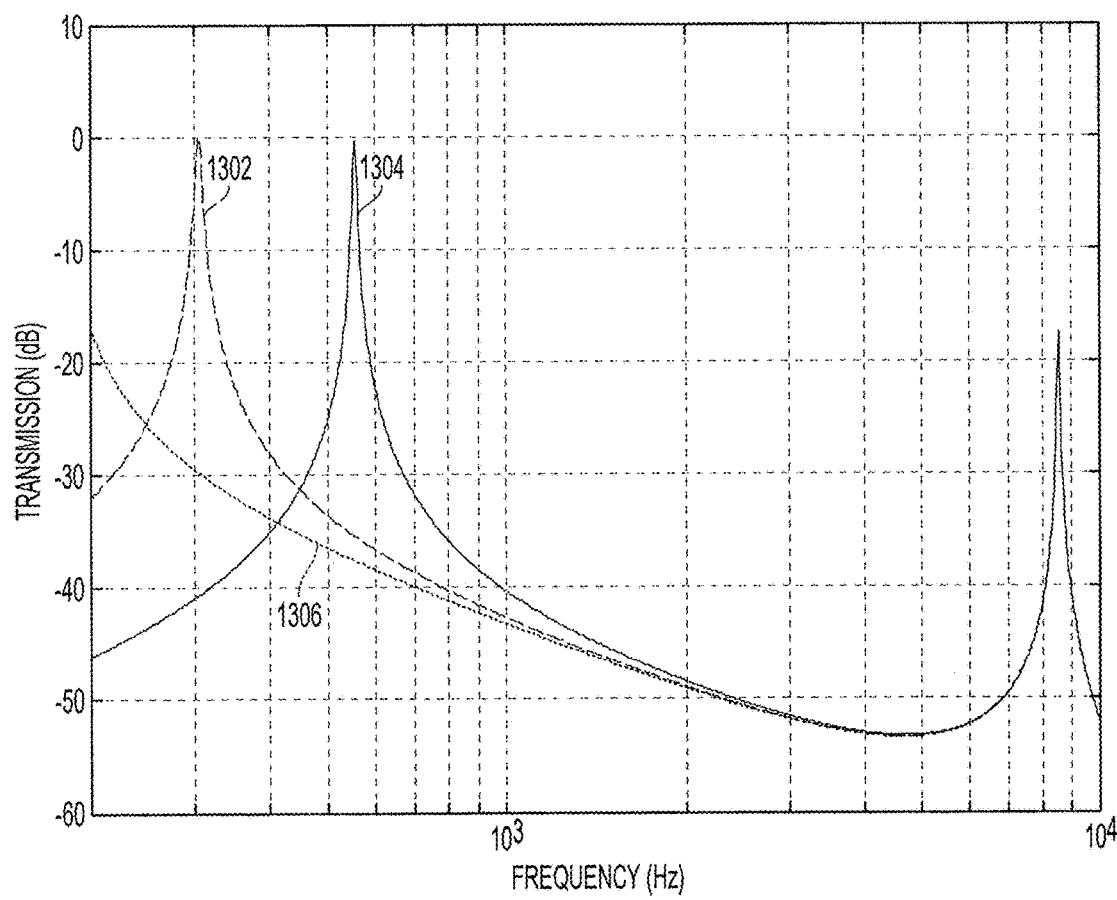
FIG. 13 is a graph of transmission as a function of frequency for the electro-acoustic circuit diagram shown in FIG. 12C, for various capacitance values of an expandable element.

Referring to FIG. 13, example transmission coefficients are shown for the electro-acoustical circuit shown in FIG. 12C, using several values of capacitance for a water-filled balloon. For the example, the balloon volume is 0.713 cm³ and the constraining tube has an inner diameter of 0.953 cm. The capacitance $C_b$ of faces 508, 512 may be estimated according to the following argument. The shape of balloon 502 on inflation may depend mainly on the pressure difference across the membrane and not on what liquid 1202 (e.g., water) balloon 502 contains. If water-filled balloon 502 is inflated to a volume comparable to that of an air-filled balloon, there may be a comparable inflation pressure. In the example, the inflation pressure is selected as 300 mbar. The capacitances $C_b$ include $3C_g$, $C_g$, and $0.3C_g$. In particular, curve 1302 represents $C_b=C_g$, curve 1304 represents $C_b=0.3C_g$ and curve 1306 represents $C_b=3C_g$. As shown in FIG. 13, the transmission is quite low up to about 2 or 3 kHz. Curves 1302 and 1304 include a low frequency resonance due to the mass of the water and the stiffness of the balloon material. In general, by filling balloon 502 with liquid 1202, system 1200 may act as a low pass filter. Presumably filling the balloon 502 with a non-Newtonian liquid (instead of water) will alter the characteristics of the curve in FIG. 13 reflecting even greater attenuation overall.

Referring generally to FIGS. 2 and 6A-13, exemplary occlusion sections 202 of the present invention may be formed to produce a predetermined sound attenuation characteristic over a frequency band, for an expanded state of one or more expandable elements 208. The predetermined sound attenuation characteristic may be produced by selecting physical parameters of occlusion section 202 (such as the material of expandable element 208, medium 228, as well as the effects of insertion element 206) in accordance with an electro-acoustical circuit model of occlusion section 202 in ear canal 108. Thus, appropriate materials and mediums may be selected that substantially match acoustical element characterizations of expandable element 208 and medium 228, to produce the predetermined sound attenuation characteristic. The predetermined sound attenuation characteristic, in general, may include a first frequency range over which sound is substantially attenuated and a second frequency range over which sound is substantially passed. Use of different non-Newtonian fluids in terms of size of particles, concentration of particles, shapes of particles, types of mixtures with other materials (such as fibers or with polyurethane to form foam), types of particles (e.g., spheres, rods, nanotubes, fibers, etc.) used and whether no particles are used will provide even more options in customizing sound attenuation characteristics unavailable to designers previously before.

It is understood that a predetermined sound attenuation characteristic may also be produced by combining multiple expandable elements 208 (with similar or different materials) filled with different mediums 228. For example, a first expandable element 208 filled with gas (to produce a high pass filter) may be coupled with a second expandable element 208 filled with a liquid (to produce a low pass filter). The combination of the two expandable elements 208 with different mediums 228 may produce a band pass filter. The combinations of different non-Newtonian fluids or non-Newtonian fluids in one expandable element and other fluids or gas in a separate expandable element may also provide further options in providing customized predetermined sound attenuations characteristics.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A method of attenuating sound from one end of a chamber or conduit to another end of the chamber or conduit, comprising:
   providing a open-ended conduit or chamber; and
   forming a closed conduit or chamber using at least a first member comprising a first expandable element that includes a non-Newtonian fluid where the first member is placed at an open end of the conduit or chamber and where the non-Newtonian fluid provides an variable attenuation response in response to a variable ambient sound pressure level stimulating an outer surface of the first member, wherein the non-Newtonian fluid increases in viscosity and hardness as the variable ambient sound pressure level increases, thereby causing an increase in attenuation of sound corresponding to the variable ambient sound pressure level as the variable ambient sound pressure level increases; and
   providing a second member co-located with the first member, wherein the second member comprises a second expandable element that includes a different non-Newtonian fluid than the non-Newtonian fluid included in the first member, wherein the first and second expandable elements combine to produce a band pass filter.

2. The method of claim 1, wherein the non-Newtonian fluid is a shear thickening fluid or a dilatant fluid and wherein attenuation response such that a greater ambient sound pressure level stimulating the outer surface of the first member causes a greater level of attenuation.

3. The method of claim 1, wherein the non-Newtonian fluid comprises carrier liquid and rigid colloidal particles.

4. The method of claim 1, wherein the non-Newtonian fluid comprises carrier fluid selected from the group of water, ethylene glycol (EG) and the non-Newtonian fluid further comprises particles selected from the group comprising silica, titanium, oxide, calcium carbonate, cornstarch, synthetically occurring minerals, naturally occurring minerals, polymers, or a mixture of any of the aforementioned particles.

5. The method of claim 1, wherein the non-Newtonian fluid is a shear thickening fluid containing composites using rubber as a precursor and adding a catalyzing agent.

6. The method of claim 1, wherein the first member is formed using a shear thickening fluid combined with an open cell polyurethane to form a foam-shear thickening fluid composite.

7. The method of claim 1, wherein the non-Newtonian fluid is a non-particle based shear thickening fluid.

8. A sound attenuating device, comprising:
   an occluding element configured to form a closed conduit or chamber upon insertion into an open end of the conduit or chamber, wherein the occluding element includes a first expandable element and a second expandable element;
   a non-Newtonian fluid forming at least a portion of the first expandable element of the occluding element where the non-Newtonian fluid provides a variable attenuation response in response to a variable sound pressure level impinging an outer surface of the occluding member, wherein the non-Newtonian fluid increases in viscosity and hardness as the variable ambient sound pressure level increases, thereby causing an increase in attenuation of sound corresponding to the variable ambient sound pressure level as the variable ambient sound pressure level increases; and a different non-Newtonian fluid forming at least a portion of the second expandable element, wherein the different non-Newtonian fluid is different from the non-Newtonian fluid, wherein the first and second expandable elements combine to produce a band pass filter.

9. The device of claim 8, wherein the non-Newtonian fluid is a shear thickening fluid or a dilatant fluid and where the non-Newtonian fluid comprises carrier liquid and rigid colloidal particles.

10. The device of claim 8, wherein the non-Newtonian fluid comprises carrier fluid selected from the group of water, ethylene glycol (EG) and the non-Newtonian fluid further comprises particles selected from the group comprising silica, titanium, oxide, calcium carbonate, cornstarch, synthetically occurring minerals, naturally occurring minerals, polymers, or a mixture of any of the aforementioned particles.

11. The device of claim 8, wherein the non-Newtonian fluid is a shear thickening fluid containing composites using rubber as a precursor and adding a catalyzing agent.

12. The device of claim 8, wherein the first member is formed using a shear thickening fluid combined with an open cell polyurethane to form a foam-shear thickening fluid composite.

13. The device of claim 8, wherein the non-Newtonian fluid is a non-particle based shear thickening fluid.

14. The device of claim 8, wherein the non-Newtonian fluid comprises anisotropic particles, spherical particles, or at least one of fibers, rod-like elements, nanoparticles, or nano-tubes.

15. The device of claim 8, wherein the non-Newtonian fluid comprises electrorheological fluids composed of dispersions of electrically polarizable particles in an insulating fluid that increases in shear viscosity when exposed to an electric field or the non-Newtonian fluid comprises magnetorheological fluids composed of dispersions of magnetic particles in an inert or non-magnetic carrier liquid that increases in shear viscosity when exposed to a magnetic field.

16. The device of claim 8, wherein the first member comprises a balloon filled with the non-Newtonian fluid.

17. The device of claim 8, wherein the sound attenuating device is an earpiece configured to occlude an ear canal with the occluding element.

18. An earphone or an earpiece, comprising:
    an occluding element configured to form a closed conduit or chamber upon insertion into an open end of the conduit or chamber or to substantially enclose an ear from an ambient environment, wherein the occluding element includes a first expandable element and a second expandable element;
    a non-Newtonian fluid forming at least a portion of the first expandable element of the occluding element where the non-Newtonian fluid provides an increasing attenuation response in response to an increasing sound pressure leveling impinging an outer surface of the occluding member, wherein the non-Newtonian fluid provides the increasing attenuation response by increasing in viscosity and hardness in response to the increasing sound pressure leveling; and
    a different non-Newtonian fluid forming at least a portion of the second expandable element, wherein the different non-Newtonian fluid is different from the non-Newtonian fluid, wherein the first and second expandable elements combine to produce a band pass filter.

19. The earphone or earpiece of claim 18, where an external portion of the earphone configured to cover the ear is made at least partially of the non-Newtonian fluid.

20. The earphone or earpiece of claim 18, wherein the non-Newtonian fluid enables the maintenance of situational awareness in a passive manner without the use of active components or electronics and only using the chemical or physical characteristics of the non-Newtonian fluid to configure a range of situational awareness exhibited by the earphone or earpiece.

* * * * *